United States Patent
Itskovich et al.

(10) Patent No.: US 6,437,564 B1
(45) Date of Patent: Aug. 20, 2002

(54) ESTIMATE OF TRANSVERSAL MOTION OF THE NMR TOOL DURING LOGGING

(75) Inventors: Gregory Boris Itskovich; David Beard; Arcady Reiderman, all of Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/846,971

(22) Filed: May 1, 2001

(51) Int. Cl.⁷ .................................................. G01V 3/00
(52) U.S. Cl. ........................................ 324/303; 324/300
(58) Field of Search ................................. 324/303, 300, 324/306, 307, 310, 311, 312, 314, 318, 322

(56) References Cited

U.S. PATENT DOCUMENTS

| | | | | |
|---|---|---|---|---|
| 5,291,137 A | * | 3/1994 | Freedman | 324/303 |
| 5,389,877 A | * | 2/1995 | Sezginer et al. | 324/303 |
| 5,834,936 A | * | 11/1998 | Taicher et al. | 324/303 |
| 6,018,243 A | * | 1/2000 | Taicher et al. | 324/300 |

FOREIGN PATENT DOCUMENTS

| | | | |
|---|---|---|---|
| EP | 0977057 A2 | * | 2/2000 |
| WO | WO99/36801 | * | 7/1999 |

* cited by examiner

Primary Examiner—Louis Arana
(74) Attorney, Agent, or Firm—Madan, Mossman & Sriram, P.C.

(57) ABSTRACT

The static magnetic field of a permanent magnet used in an NMR tool moves with the tool. NMR measurements made with a moving tool are affected by incomplete polarization of the nuclear spins in the region where the Larmor frequency of static field matches the RF signal frequency. Simulation results show that the in-phase and quadrature components of spin echo signals are affected by the velocity of lateral motion of a logging tool in a borehole. A phase drift indicator is obtained by summing the quadrature and in-phase components over a window and taking the ratio of the windowed sums. The phase drift indicator shows an increase with time. In a tool with a gradient magnetic field, the phase drift indicator increases with time even for no tool motion. The reduction in magnitude of spin echo data due to tool motion alone may be obtained by comparing the magnitude of simulated echoes with and without tool motion.

15 Claims, 5 Drawing Sheets

ESTIMATE OF TRANSVERSAL MOTION OF THE NMR TOOL DURING LOGGING

BACKGROUND OF THE INVENTION

1. Field of the Invention

The invention is related to the field of Nuclear Magnetic Resonance ("NMR") apparatus and methods. More specifically, the invention relates to detecting and estimating the effect of transversal motion of the NMR tool used in oil well logging on the signal-to noise ratio by using both in-phase and out-phase measurements of spin echoes.

2. Description of the Related Art

NMR has applications in various fields from medical applications to oil well logging applications. In oil well testing, NMR is used to determine, among other things, the porosity of the material, the amount of bound liquid in the volume, permeability, and formation type, as well as oil content.

A current technique in wellbore logging employs an NMR tool to gather information during the drilling process. This technique is known as logging while drilling (LWD) or measuring-while-drilling (MWD) and requires the NMR tool to be included as part of the drilling bottom hole assembly. This process greatly increases speed at which information is gathered and consequently reduces the cost of acquiring downhole information. This tool can be, as an example, one that is outlined in U.S. Pat. No. 5,280,243, entitled, "System For Logging a Well during the Drilling Thereof", granted to Miller. The device disclosed therein includes a permanent magnet which induces a static magnetic field into the surrounding volume. In addition, an antenna, which is aligned orthogonal to this magnet, has the purpose of introducing radio frequency (RF) pulses into the region. The same or another antenna is used to receive signals returning from the volume.

Typically, in the presence of only the permanent magnet, nuclear spins will align either parallel or anti-parallel to the static magnetic field, creating a net overall magnetic polarization, called a bulk magnetization. An electric RF pulse sent through this antenna induces another magnetic field in the region. If this induced magnetic field is perpendicular to the field of the permanent magnet, then the induced magnetic field pulse reorients the direction of individual spins perpendicular to the direction of the static field and to the direction of the induced magnetic field. Upon removing the RF pulse, the spins will relax by realigning to their original orientation, along the axis of the static field. The relaxation of the spins to their original orientation occurs over a characteristic time interval, which is known as the spin-lattice relaxation time, $T_1$. This relaxation induces a voltage in the receiver antenna.

Spins oriented perpendicular to the static field undergo other motions which can be measured. The spin vector relaxes out of this transverse direction with a characteristic time known as the spin-spin relaxation time or transverse relaxation time, $T_2$. Typically, a pattern of RF pulses can be used to determine $T_2$. A commonly used pulse pattern is known as the Carr-Purcell-Meiboom-Gill (CPMG) sequence. The CPMG is comprised of one pulsed magnetic field applied in a direction orthogonal to the static magnetic field followed by several pulses applied at preset time intervals in a direction mutually perpendicular to both the direction of the first pulse and the direction of the static magnetic field. The first pulse of the CPMG sequence is known as the A-pulse, and typically occurs over a short time scale with respect to the relaxation time, $T_2$. In response to the A-pulse, the spin vectors of the nuclei will align along a common direction in the plane that is perpendicular to the static magnetic field. When an individual spin vector is placed perpendicular to an applied external field, it will precess around the field with a frequency of precession known as the Larmor frequency, which is related to the strength of the applied field. Due to inhomogeneities in the magnetic field, some spins will precess faster while other spins will precess more slowly. Thus, after a time long compared to the precession period, and short compared to $T_1$, the spins will no longer be precessing in phase. The diffusion of the phase of the precession takes place over a time scale $T_2^*$. For an acceptable observation, it is best to have $T_2 >> T_2^*$.

The B-pulse of the CPMG sequence lasts twice the duration of the A-pulse and is also short compared to precession periods and to relaxation time. Applying the B-pulse gives the nuclear spins an axial rotation of 180 degrees from their immediately previous orientation. In the new orientation after applying the B-pulse, the spins, which were previously diverging from their common orientation due to the A-pulse, are now returning towards this orientation. In addition, by inverting the spatial relation of leading and lagging precessors, the spins are now moving back into phase. As the spins realign, the cumulative effect of this alignment causes a spin echo. The sudden magnetic pulse of the spin echo induces a voltage in the receiving antenna.

Once the spins have realigned and produced the spin echo, they will naturally lose phase again. Applying another B-pulse flips the spin orientation another 180 degrees and sets up the condition for another spin echo. By a using a train of B-pulses, the CPMG pulse pattern creates a series of spin echoes. The amplitude of the train of spin echoes decreases according to the relaxation time, $T_2$. Knowledge of $T_1$ and $T_2$ gives necessary information on the properties of the material being examined.

Measurements made for $T_1$ and $T_2$ require that the NMR measuring device remain stationary over the proper time period. However, a typical measurement period can last over 300 msec. Over a testing period that is sufficiently long, the measuring device will be susceptible to motion from its initial position. At the beginning of the testing period, the permanent magnet might polarize spins of nuclei remaining within a given volume, which can be seen in FIG. 6 as the shaded volume 20a. It is necessary for a certain amount of time to lapse for these spins to polarize completely. If the NMR tool moves during this time, the volume 20a changes its position as shown in FIG. 7. At this new position, the volume 20a contains only a portion of the original volume shown in FIG. 6, and the receiving antenna will necessarily record unsaturated spins from the new volume. Instead, the new volume contains spins that are not properly aligned to the static field. This effect is typically referred to as "moving fresh spins in" and is a source of error in the detection signal. As an example, the measurement may yield a bound fluid volume (BFV) that is higher than the amount that is actually present in the region.

Several methods have been proposed to detect motion in order to address the problems this motion introduces. Among these methods include use of strain gauges, an ultrasonic range finder an accelerometer, or a magnetometer. These arrangements are described in PCT Application Number PCT/US97/23975, titled "Method for Formation Evaluation While Drilling" filed Dec. 29, 1997. These motion detection devices help to set a threshold to establish the quality of the recorded data. However, they do not provide a means to make corrections which might maintain the quality of the data.

Another proposed device is detailed in European Patent Application 99401939.6, titled "Detecting tool motion effects on nuclear magnetic resonance measurements." This application uses different geometries and magnetic gradients to measure tool motion. Given the same motion rates of the NMR tool, the signals from two regions of differing applied magnetic gradients will decay at different rates. In the application, setting up an apparatus with two magnetic field gradients makes it possible to obtain both signals and thereby determine the motion speeds and the necessary corrections. Similar information can be derived by measuring spin-echoes in two radially-adjacent regions.

Different magnetic field gradients are easily achieved by placing several permanent magnets in various spatial arrangements with respect to one another. For example, shortening the distance between the north poles of magnets can increasing the magnetic field gradient. NMR signals received from regions with higher magnetic field gradients are more sensitive to motion than those received from regions with lower magnetic field gradients. Specifically, when the NMR tool is in motion, a signal received from a high gradient region decays at a rate more slowly than a signal coming from a low gradient region. Comparing the relative decay rates of signal strengths from each region allows a determination of the amount of motion of the NMR tool. Erroneous calculations may be introduced, since the low gradient region and the high gradient region are separate volumes.

Another method that has been taught is to truncate the pulse sequence to the order of 10 milliseconds rather than 300 msec. This procedure is taught in U.S. Pat. No. 5,705,927 issued to Kleinberg. At such short times, the quality of the data remains acceptable. However, not always will there be enough data to extrapolate values for $T_2$.

There is a need for a method of determining from the NMR signals themselves indications of when the data quality is likely to be acceptable. The present invention satisfies this need.

SUMMARY OF THE INVENTION

The present invention is a method of making Nuclear Magnetic Resonance (NMR) measurements. A magnet on an NMR tool is used to generate a static magnetic field in a volume containing materials sought to be analyzed. A radio frequency (RF) transmitter antenna on the NMR tool induces a RF magnetic field in the volume and excites nuclear spins of nuclei therein, the RF magnetic field being substantially orthogonal to the static field in said volume. When the tool is subject to transversal motion, the spin-echo signals are affected by the tool motion. A receiver antenna is used for receiving in-phase and quadrature components of signals from said excited nuclei. A phase drift indicator may be determined from the in-phase and quadrature components of said signals. This phase drift indicator is diagnostic of tool motion.

The method of the present invention may be used with any of a number of different types of logging tools having different magnet and coil configurations. These include tools with opposed magnets, and transverse dipole magnets.

The method of the present invention may be used with conventional CPMG sequences or with modified sequences designed for reduced power consumption having B pulses that are less than 180°. Phase alternated pairs of measurements may be used to reduce the effects of ringing.

The phase drift indicator is preferably determined as the ratio of a windowed sum of the magnitudes of the quadrature component signals to the windowed sum of the magnitudes of the in-phase component signals.

DESCRIPTION OF THE PREFERERED EMBODIMENT

An NMR instrument suitable for use with the present invention is described in U.S. Pat. No. 5,757,186 to Taicher et al, the contents of which are fully incorporated herein by reference. The device in Taicher employs a magnet configuration in which the static field is substantially radial in the region of examination. The use of the apparatus disclosed therein is not intended to be a limitation and any suitable NMR device designed for MWD operations may be used for the purpose. For example, the method of the present invention may also be used with other commonly used configurations in which the magnet and the RF coil are transverse dipoles.

Figure 1:
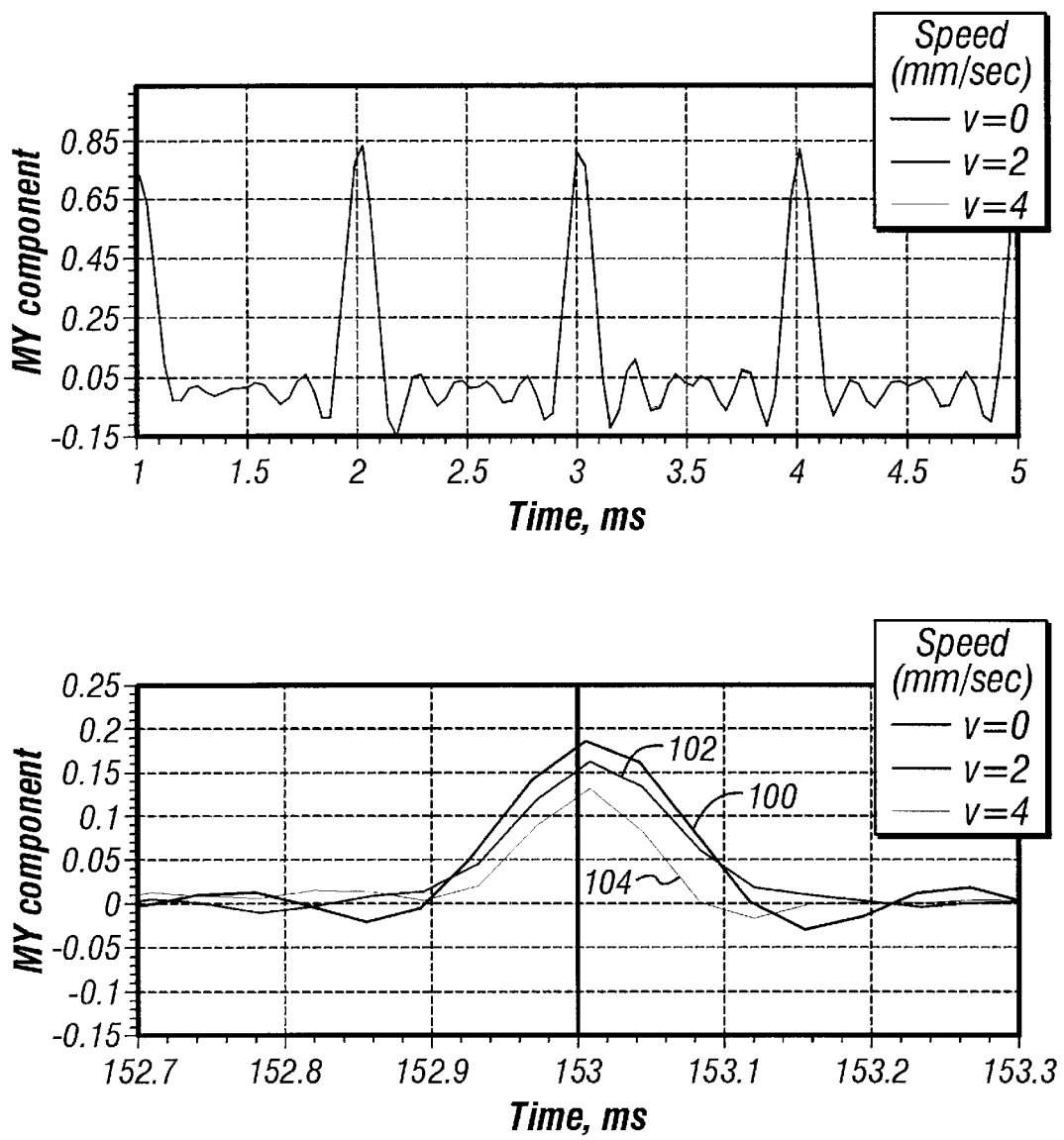
FIG. 1 shows a graph of in-phase echo spin signals in response to an idealized CPMG pulse for transversal velocities at v=0, 2, and 4 mm/sec for time from t=0 msec to t=5 msec and then for time near t=153 msec.

Mathematical modeling of the nuclear response signal to an idealized CPMG pulse train can simulate the effect transversal movement of the NMR tool has on the data results. The simulation in this invention uses an idealized CPMG signal, comprised of infinitely short A and B pulses, and assumes no $T_1$ or $T_2$ relaxation times. FIG. 1 shows a graph of the in-phase components ($M_y$) of the spin echo signals as a response to this idealized signal. The in-phase components are measured along the direction in which the nuclear spins align after the application of the B-pulse. The different signal responses are shown for transversal speeds of v=0, 2, and 4 mm/sec of the logging instrument. As is expected, the decay of the peak signals becomes pronounced at higher velocities. FIG. 1 shows an increased decay when the NMR tool moves at a velocity of v=4 mm/sec. For instance, at a time of t=153 milliseconds, the peak signal is reduced from approximately 0.18 at v=0 mm/sec to approximately 0.13 at v=4 mm/sec, as shown in curve 104.

Figure 2:
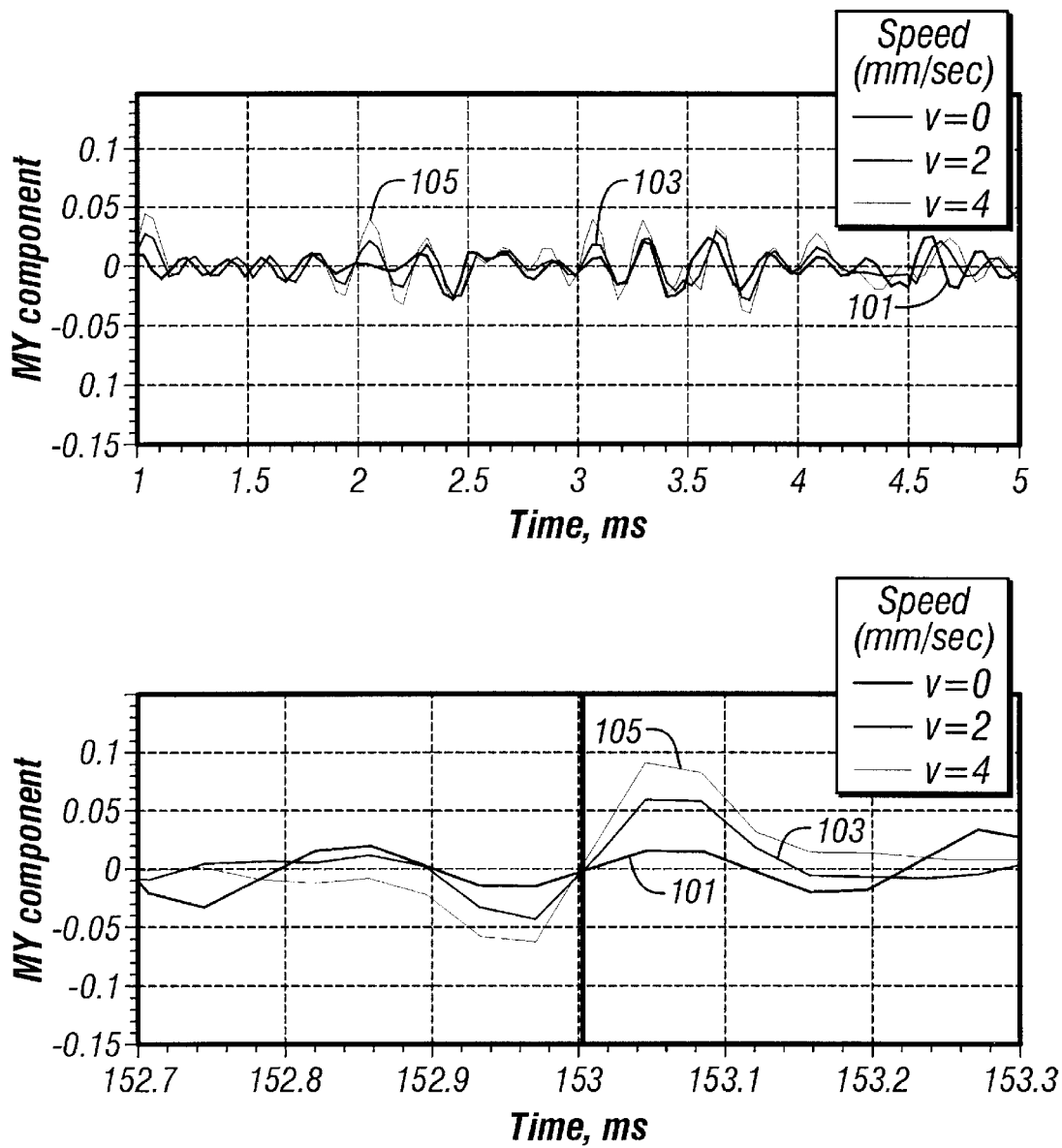
FIG. 2 shows a graph of out-phase echo spin signals in response to an idealized CPMG pulse for transversal velocities at v=0, 2, and 4 mm/sec for time from t=0 msec to t=5 msec and then for time near t=153 msec.

FIG. 2 shows a corresponding growth in the amplitude of the out-of-phase or quadrature components of the spin echo signal at velocities of v=0, 2, and 4 mm/sec over the same time scale as used in FIG. 1. The out-phase components are measured in a direction which is perpendicular to both the direction of the static field and to the direction of the original orientation of the nuclear spin vector after the application of the A-pulse. Although the amplitudes of the out-phase peaks are small compared to the peak strength of the in-phase components at t=0, they grow over time, with the growth rate corresponding to velocity. FIG. 2 shows that the out-phase components are greatest for the transverse velocity of v=4 mm/sec. A comparison of the amplitudes at a time of t=153 milliseconds of curve 104 from FIG. 1 and of curve 105 from FIG. 2 shows that at a velocity of v=4 mm/sec, the out-phase components are on the same order of magnitude as the in-phase components.

Figure 3:
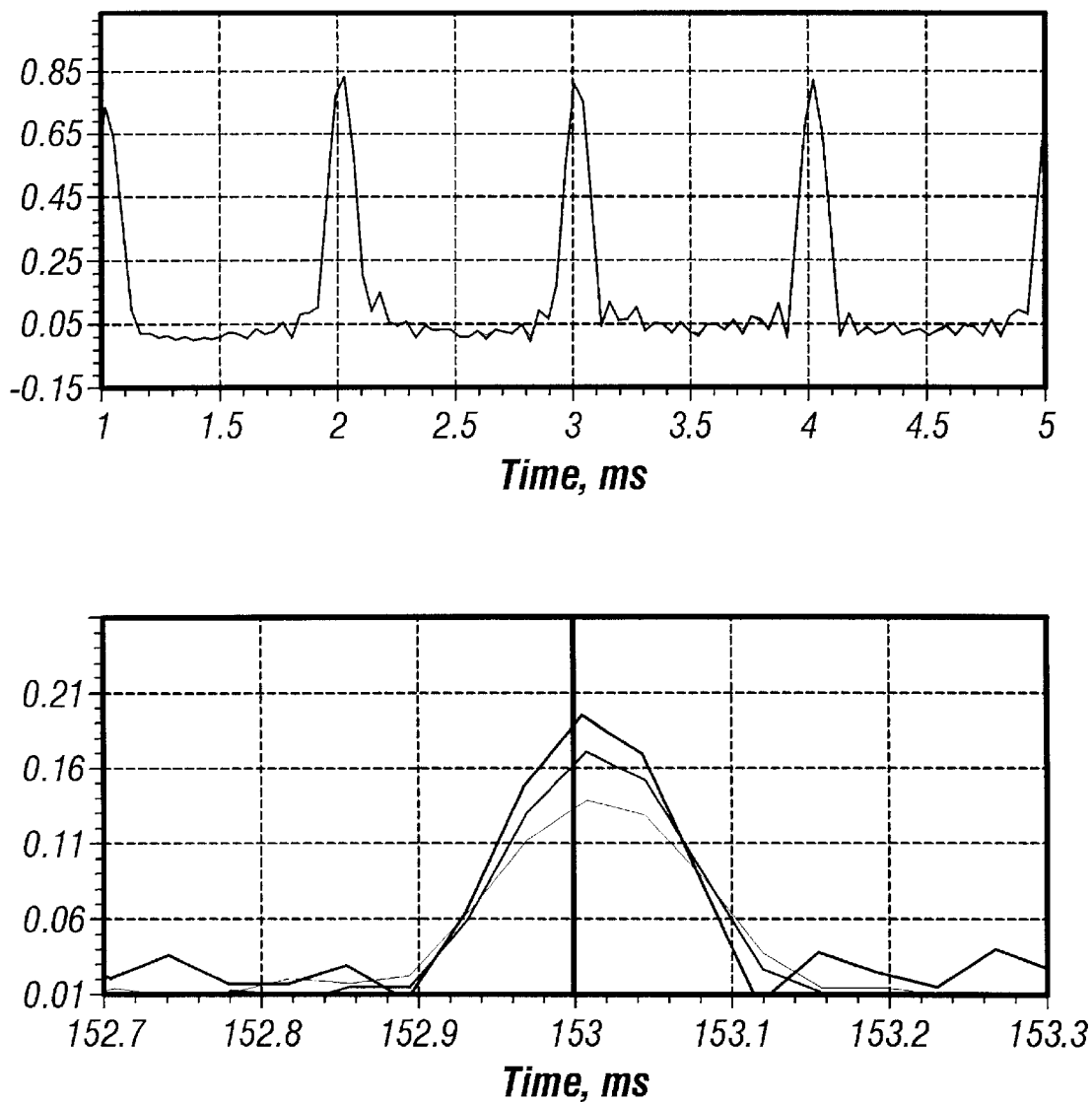
FIG. 3 shows a graph of the magnitude of the magnetization vector, denoted $M_{xy}$, to an idealized CPMG pulse for transversal velocities at v=0, 2, and 4 mm/sec for time from t=0 msec to t=5 msec and then for time near t=153 msec.

FIGS. 3 shows the effect of transversal motion on the magnitude of the magnetization vector $M_{xy}$, which is the combined effects of the out-phase and in-phase components seen in FIGS. 1 and 2. The effects of motion appear in both the decay of the in-phase peaks as well as in the growth of the out-phase peaks. As an example, at a time of t=153 milliseconds, for v=4 mm/sec, the out-phase peaks have nearly the same amplitude as the in-phase peaks and can therefore lead to erroneous results. As would be expected, the effect is more pronounced for the greater transversal velocities. The growth of out-phase peaks obscures information on the decay of the in-phase peaks. In order to quantify the effects of transversal motion, an equation (Eq. 1) is introduced. This equation defines a phase drift indicator which can then be used to set up a test of the quality of the recorded data.

$$\psi = \frac{\left|\sum_{i=nc-m}^{i=nc} M_{xi}\right| + \left|\sum_{i=nc+1}^{i=nc+m} M_{xi}\right|}{\left|\sum_{i=nc-m}^{i=nc+m} M_{yi}\right|} \quad (1)$$

The phase drift indicator, $\psi$, is a ratio of a summation of out-phase components to a summation of in-phase components. In a preferred embodiment of the invention, the summation is one of absolute values and in alternate embodiments of the invention, other types of summation, such as the sum of squared values, may be used. The indicator is obtained by recording in digital format the in-phase and out-phase components of the spin echo signals. The digitization window is ideally centered on a spin echo peak and is comprised of 2 m+1 data points. In the phase drift equation, the summation of the out-phases components is divided into two summations, one for the components prior to the moment of the spin echo peak and one for the components after the moment of the peak. The indicator grows corresponding to the growth of the out-phase components and more specifically measures the comparative magnitudes of the in-phase and out-phase signals.

Figure 4:
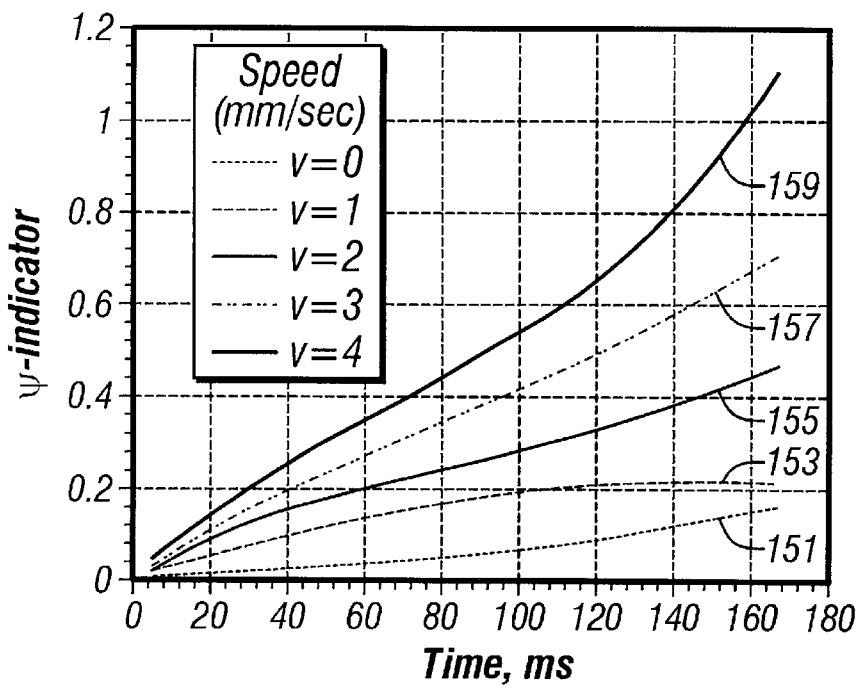
FIG. 4 represents the results of calculations of the phase drift indicator shown in equation 1 with transversal speeds of v=0, 1, 2, 3, and 4 mm/sec for the well logging instrument under an idealized CPMG pulse train.

FIG. 4 shows the results of the calculations of the phase drift indicator measurements made over a period of time from 0 msec to about 180 msec for integral transversal velocities from v=0 to v=4 mm/sec. As an example, at times near 0 msec, FIG. 3 shows peaks with high signal-to-noise ratio for $M_{xy}$, meaning that the in-phase components are much stronger than the out-phase components at this time for all velocities. Comparing to FIG. 4 at these early times, the value of $\psi$ is a correspondingly small amount regardless of velocity. An example shows how the phase drift indicator corresponds with differences in in-phase and out-phase components. Examining curve 101 in FIG. 2 which is at v=0 mm/sec near t=153 msec, the peak value of this component has not grown appreciably compared to its value near t=0 msec. In this case, $\psi$ in FIG. 4 remains small at later times, rising to less than 0.2, as seen with curve 151. At higher velocities, out-phase and in-phase peaks can become equal in magnitude at later times. Curve 105 in FIG. 2 shows a spin-echo graph associated with a faster velocity v=4 mm/sec. The peak value near t=153 msec reaches 0.1, which is close to the peak value for in-phase components at the same time for v=4 mm/sec shown in FIG. 1. The phase drift indicator reflects this situation. Curve 159 in FIG. 4 shows the phase-drift indicator for v=4 mm/sec. At t=150 msec, curve 159 has a value of 0.9 and is rising. The shape of the lines compares reasonably to what one would expect, with the phase drift indicator growing at a faster rate for the greater transversal velocity. The simulations were carried out for a tool with a gradient field and it can be seen that in the presence of a gradient field, the phase drift indicator can be non-zero even for zero transversal tool motion. On the other hand, in a zero gradient logging tool, the phase drift indicator should be zero at all times.

Figure 5:
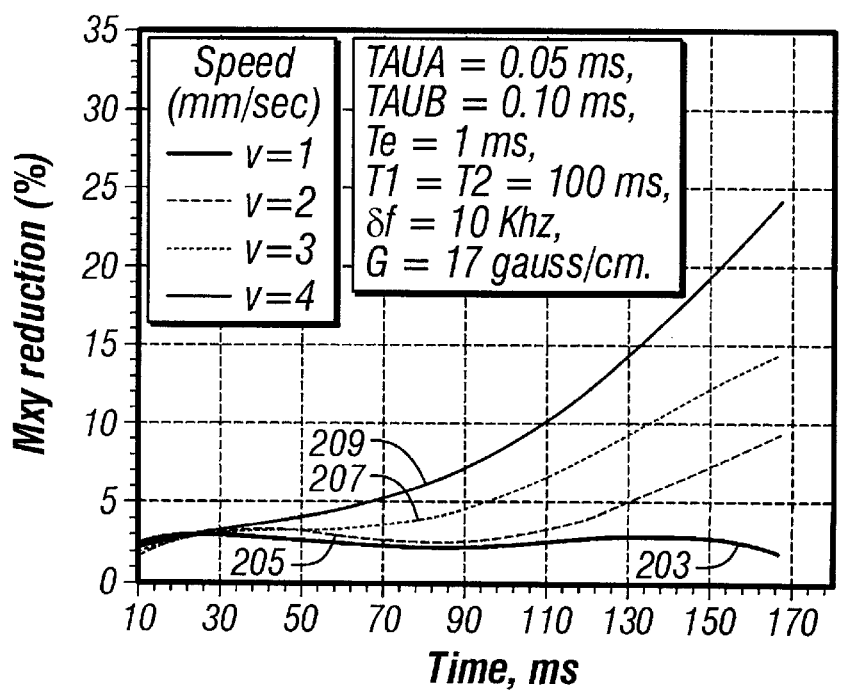
FIG. 5 shows the reduction of the magnetization vector $M_{xy}$ due to transversal speeds of v=0, 1, 2, 3, and 4 mm/sec.
Figure 6:
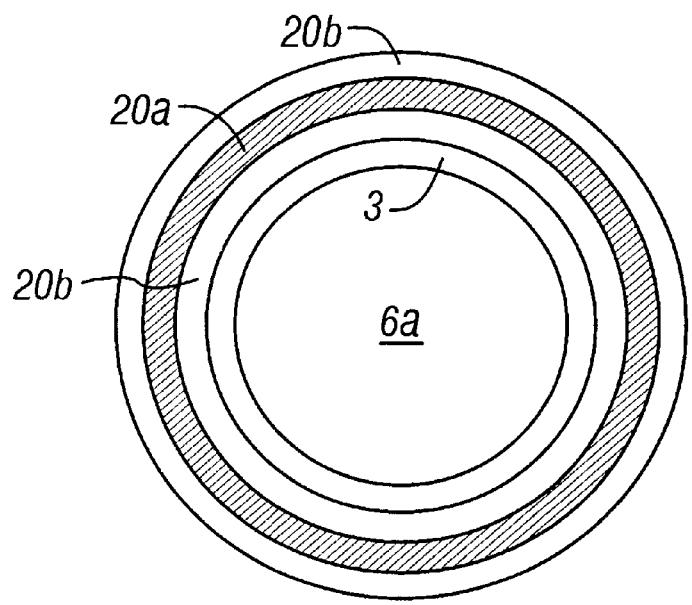
FIG. 6 shows the ideal alignment of an NMR tool in a region, with the shaded region representing the volume in which total saturation due to the magnet occurs.
Figure 7:
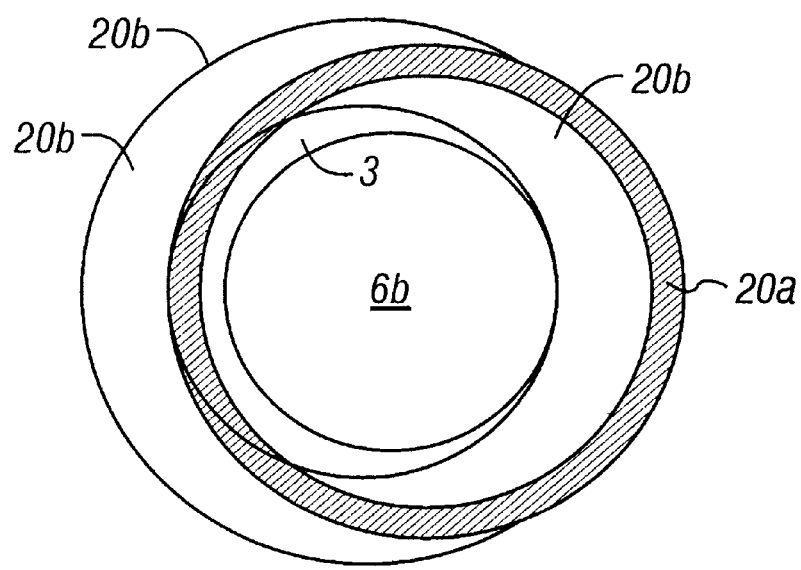
FIG. 7 shows an off-center alignment of an NMR tool in a region, with the shaded region representing the volume in which total saturation due to the magnet occurs.

FIG. 4 can be used to establish a threshold for quality, via the phase drift indicator. In a preferred embodiment of the invention, the phase drift indicator would be calculated at each spin-echo peak and compared to a preset threshold value. FIG. 5 shows the percentage of reduction of the magnitude of the signal $M_{xy}$ due to the transversal movement of a well logging instrument alone. This percentage is obtained by comparing the reduction in magnitude of the signal for a given speed of lateral movement with that which results when there is no lateral movement. In FIG. 5, curve 203 represents the reduction with v=1 mm/sec. Even at later times, the effect remains small. Curve 209 represents the reduction of $M_{xy}$ due to a transverse velocity of v=4 mm/sec. This curve grows at later times, such that at t=150 msec there is a 20% reduction in $M_{xy}$.

There is a direct correspondence between the curves 153, 155, 157, and 159 in FIG. 4 and curves 203, 205, 207, 209 in FIG. 5. Those practiced in the art can choose values from FIG. 4 and FIG. 5 to obtain a reasonable assessment of the desired level for this threshold. For example, if $\psi$ is equal to 0.6 at 110 msec, as shown for the curve 159 in FIG. 4, then the error in the magnitude of the corresponding echo will be 10% as shown in curve 209 in FIG. 5. This can be used to correct the magnitude of measured spin-echo signals before further processing.

The method of the present invention has been discussed above using an example of a CPMG sequence. U.S. Pat. No. 6,163,153 to Itskovich et al, the contents of which are fully incorporated here by reference, teaches the use of a modified pulse sequence in which the B-pulse is less than 180°, and may have an associated tipping angle between 90° and 180°. The method of the present invention may also be used with such modified pulse sequences. When used with such modified sequences, the effect of tool motion is subject to two opposing effects. First, the overall sequence may be acquired in a shorter time, resulting in less effects of tool motion. Second, the bandwidth of the B pulse is closer to the bandwidth of the A pulse, so that the effects of "moving fresh spins in" are greater.

As would be known to those versed in the art, a common problem with analysis of NMR measurements is that the signal detected by the antenna includes a parasitic, spurious ringing that interferes with the measurement of spin-echoes. To reduce the effects of this ringing, a so-called phase-alternated-pulse sequence is commonly used.

Such a sequence is often implemented as $$RFA_{\pm x}\text{-}\tau\text{-}n\cdot(RFB_y\text{-}\tau\text{-}echo\text{-}\tau)\text{-}TW \quad (2)$$

where $RFA_{\pm x}$ is an A pulse, usually 90° tipping pulse and RFB is a refocusing B pulse. The ± phase of RFA is applied alternately in order to identify and eliminate systematic noises, such as ringing and DC offset through subsequent processing. By subtracting the echoes in the−sequence from the pulses in the adjoining+sequence, the ringing due to the 180° is suppressed. The method of the present invention may also be used with such phase alternated pairs.

The method of the present invention may be used with logging tools that are conveyed on a wireline, with measurement while drilling (MWD) tools that are conveyed on a bottom hole assembly by a drillstring or on coiled tubing, or in a logging while tripping tool carried on a bottom hole assembly.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of making Nuclear Magnetic Resonance (NMR) measurements comprising:
   (a) using a magnet on an NMR tool to generate a static magnetic field in a volume containing materials sought to be analyzed;
   (b) using a radio frequency (RF) transmitter antenna on the NMR tool for inducing a RF magnetic field in said volume and exciting nuclei therein, said RF magnetic field substantially orthogonal to the static field in said volume;
   (c) using at least one receiver antenna on the NMR tool for receiving in-phase and quadrature components of signals from said excited nuclei; and
   (d) determining a phase drift indicator from said in-phase and quadrature components of said signals.

2. The method of claim 1 wherein said volume is located in a subsurface formation and the NMR tool is conveyed on a borehole in said subsurface formation.

3. The method of claim 2 wherein said static field in said region of investigation has a direction that is selected from (i) substantially parallel to a longitudinal axis of the borehole, (ii) substantially orthogonal to a longitudinal axis of the borehole, (iii) radial relative to the borehole, and, (iv) circumferential relative to the borehole.

4. The method of claim 2 wherein using said transmitter antenna further comprises exciting the transmitter with a pulsed RF current.

5. The method of claim 4 wherein said pulsed RF current further comprises a carrier signal having a carrier frequency.

6. The method of claim 5 wherein said pulsed RF current further comprises modulating said carrier signal with a pulse sequence selected from (i) a CPMG sequence, and, (ii) a modified CPMG sequence.

7. The method of claim 2 wherein determining said phase drift indicator further comprises:
   (i) digitizing said in-phase and quadrature components of said signals,
   (ii) determining a sum over a window of said in-phase and quadrature component of said signals, and
   (iii) determining said phase drift indicator as a ratio of the summed quadrature and summed in-phase signals.

8. The method of claim 7 wherein said window is centered on a spin ech signal.

9. The method of claim 7 wherein said sum is selected from (A) a sum of squared values, and, (B) a sum of absolute values.

10. The method of claim 2 wherein said static magnetic field has a gradient in said region of investigation.

11. The method of claim 5 wherein said carrier frequency is related to value of said static magnetic field in said volume.

12. The method of claim 7 wherein said tool has a velocity of lateral motion in said borehole, the method further comprising determination of a reduction in a magnitude of said signals relative to a tool having zero lateral velocity.

13. The method of claim 12 further comprising correcting said signals based upon said reduction in magnitude.

14. The method of claim 5 wherein said pulsed RF current further comprises modulating said carrier signal with a phase alternated pulse sequence selected from (i) a CPMG sequence, and, (ii) a modified CPMG sequence.

15. The method of claim 2 further comprising conveying said logging tool on one of; (i) a wireline, (ii) a drillstring, and, (iii) coiled tubing.

\* \* \* \* \*